United States Patent
Sfeir et al.

(10) Patent No.: US 7,997,138 B2
(45) Date of Patent: *Aug. 16, 2011

(54) METHOD FOR INSPECTION OF METAL TUBULAR GOODS

(76) Inventors: George M. Sfeir, Lafayette, LA (US);
Jeffrey S. Banks, Crosby, TX (US);
Dennis L. Rogers, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,053

(22) Filed: Jun. 29, 2009
(Under 37 CFR 1.47)

(65) Prior Publication Data
US 2010/0083763 A1 Apr. 8, 2010

Related U.S. Application Data

(63) Continuation of application No. 12/137,341, filed on Jun. 11, 2008, now Pat. No. 7,552,640, which is a continuation of application No. 11/849,287, filed on Sep. 1, 2007, now Pat. No. 7,401,518, which is a continuation of application No. 10/548,731, filed as application No. PCT/US2004/007010 on Mar. 8, 2004, now Pat. No. 7,263,887.

(60) Provisional application No. 60/452,907, filed on Mar. 7, 2003.

(51) Int. Cl.
*G01N 9/24* (2006.01)

(52) U.S. Cl. .................. 73/602; 73/599; 73/620; 73/625
(58) Field of Classification Search .................... 73/602, 73/599, 620, 625, 622, 629
See application file for complete search history.

(56) References Cited

U.S. PATENT DOCUMENTS

| | | | |
|---|---|---|---|
| 6,578,422 B2* | 6/2003 | Lam et al. .................. 73/622 |
| 6,622,561 B2* | 9/2003 | Lam et al. .................. 73/622 |
| 6,748,808 B2* | 6/2004 | Lam et al. .................. 73/622 |
| 6,915,244 B2* | 7/2005 | Yamano et al. .................. 703/2 |
| 7,263,887 B2* | 9/2007 | Sfeir et al. .................. 73/602 |
| 7,552,640 B2* | 6/2009 | Sfeir et al. .................. 73/602 |
| 7,620,532 B2* | 11/2009 | Tillman et al. .................. 703/2 |

* cited by examiner

*Primary Examiner* — Jacques M Saint Surin

(57) ABSTRACT

A method for predicting the performance of tubular goods includes using a computer readable three-dimensional representation of tubular good which includes computer readable measurements of discrete segments of the wall of said tubular acquired by ultrasonic detection means, along with associated data representing the position of discrete segment and optionally ovality data to predict the effect of stress conditions, including tensile, bending, collapse, burst and aging forces upon said tubular and optionally analyzing sequential inspection of the same tubular good over a period of time predict when failure is likely to occur, and to avoid failure while maximizing the use of the tubular good.

21 Claims, No Drawings

METHOD FOR INSPECTION OF METAL TUBULAR GOODS

CROSS REFERENCE TO RELATED APPLICATIONS

This application is a continuing patent application emanating from presently pending U.S. patent application Ser. No. 12/137,341 filed Jun. 11, 2008, which is a continuing patent application emanating from U.S. patent application Ser. No. 11/849,287 filed Sep. 1, 2007 (now U.S. Pat. No. 7,401,518 issued Jul. 22, 2008), which is a continuing patent application emanating from U.S. patent application Ser. No. 10/548,731 filed Sep. 7, 2005 (now U.S. Pat. No. 7,263,887, issued Sep. 4, 2007), which emanated from International Patent Application Number PCT/US04/07010 filed Mar. 8, 2004 which claims priority to the Provisional Patent Application No. 60/452,907 filed Mar. 7, 2003.

FIELD OF THE INVENTION

The invention disclosed herein relates to non-destructive inspection of tubular metal goods. More particularly the invention herein disclosed relates to a non-destructive means for determination of wall conditions, in particular wall thickness data, of tubular metal goods by use of ultrasonic detection apparatus. With additional specificity the invention disclosed herein relates to an improved method of collecting, storing, displaying and otherwise utilizing information resulting from ultrasonic detection of the wall of metal tubulars. With even more specificity the invention herein disclosed relates to the use of ultrasonic means to acquire incremental data representing small, discrete sections of a tubular wall in association with three-dimensional positional data pertaining to each small, discrete section, so that the wall of a metal tubular (or portions thereof) can be displayed, imaged, examined and utilized in simulative/comparative programs as a three-dimensional object.

BACKGROUND OF THE INVENTION

In many applications inspection of metal tubular goods for the presence of possible defects is highly desirable and/or required. Inspection of metal tubulars is common in, for instance, the oil and gas exploration and production industry, in refineries and/or in chemical and other plants, where the failure of such tubulars may result in serious consequences.

The art of inspecting metal tubulars for possible defects has experienced various improvements over the course of time. Early testing was rudimentary. It sometimes consisted of no more than visual inspection of the exterior of the tubular for such defects as might be seen. This method was obviously limited. Sometimes inspection might include an attempt to "ring" or "sound" the tubular. This generally involved striking the tubular with a hard object, such as a hammer, and listening to the sound the tubular produced. An abnormally "flat" tone may indicate that the tubular was cracked. This method was highly subjective and even if employed by skilled personnel was unable to detect small defects.

The need to improve inspection of metal tubulars led to other developments, such as magnetic testing. One method of magnetic testing involved magnetizing the tubular (or a portion thereof), "dusting" same with ferromagnetic powder and then visually inspecting for abnormal distribution of the powder. In another method of magnetic testing an electromagnetic coil was passed close to the surface of the tubular and various means used to determine disturbance of the induced eddy current possibly being caused by discontinuities in the tubular. Neither method was well suited for detection of small defects and/or those below the surface of the tubular, were time consuming, were largely dependent on the skill of the operator and did not produce precise data from which the effect of a condition found might be mathematically calculated.

Another attempt to improve inspection of metal tubulars was the dye penetrant method. In such method the tubular was cleaned, coated with a penetrating fluid containing dye (typically of a type which would fluoresce under certain lighting conditions), wiped and then visually inspected for surface discontinuities still containing dye. This method was not useful for detection of sub-surface defects and did not produce precise data from which the effect of a condition found might be mathematically calculated.

Another means to inspect metal tubulars is by utilization of X-rays. While x-ray represents a way to determine some defects below the surface of the tubular wall, certain defects such as thin cracks and delaminations are difficult to find by X-ray. Moreover this method of inspection does not produce precise data from which the effect of a condition found might be mathematically calculated. Because of the danger, shielding requirements, expense and limitations of this technology, its use has been limited.

An attempt to inspect metal tubular goods for wall thickness defects was represented by utilization of gamma radiation. In one method the gamma source is placed on one side of the tubular and a radiation sensor on the other side of the tubular. By measuring the decrease in radiation as it passes through the tubular an estimation of the collective wall thickness of both sides of the tubular can be made. This method has certain disadvantages, including but not necessarily limited to relative insensitivity of the sensor to small thickness changes, its inability to detect if one side of the tubular is thick and the other thin (which is not an uncommon defect, particularly in extruded tubulars) and the safety, security and administrative issues relating to utilization of radioactive sources. Moreover such inspection does not produce data from which the effect of a condition found might be calculated with mathematical precision.

In attempt to avoid the limitations of the above technology, ultrasonic technology was developed for inspection of tubular goods. In general, this technology is based on the speed of sound in metal and the fact that a sound wave will reflect ("echo") from medium interfaces. Thus by propagating a sonic wave in said metal and by measuring the time it takes for echos of that wave to return from an interface, it is possible to determine the precise distance to said interface. Such interface may, of course, be the opposite wall of the tubular. Accordingly by use of ultrasonic means precise wall thickness of a tubular at an area may be determined. In order to determine the wall thickness of a tubular about the whole area of the tubular, the tubular is typically rotated about its axis and advanced longitudinally in relation to an ultrasonic head which periodically "fires" and effectively samples wall thickness under the head at the time. As the tubular advances a stream of data points, each one representing a wall thickness measurement is generated. Typically the data resulting from such testing is displayed in two-dimensional form, as a numeric table or as a line on a graph (representing wall thickness at a position on the length of the tubular). Out-of-range values can be detected either by human reading the table or graph, or by machine (computer) detection of out of range values. From such data the general location of a suspected defect along the length of tubular, its magnitude and direction (whether too thin or too thick) can be determined and the tubular joint marked for acceptance, rejection or repair, but said data was not useful for substantial purposes therebeyond. Namely, without three-dimensional data as to both the defect and the remainder of the tubular, the effect that defect might have concerning performance of the tubular could not be calculated with mathematical precision.

The invention disclosed herein relates to improved method to acquire, collect, assemble, store, display and/or utilize data stemming from ultrasonic inspection of tubular goods, not only for a determination for the presence or absence of defects, but so that data from the inspection may be used to calculate projected performance of the tubular with a mathematical precision not previously available by non-destructive evaluation of the tubular.

OBJECTS OF THE INVENTION

The general object of the invention disclosed herein is to provide an improved means for collection, assembly, storage, display, analyze and other utilization of information derived from ultrasonic inspection of tubular goods. A particular object of the invention is associate data representing incremental ultrasonic measurements of wall of discrete, small sections of a tubular with three-dimensional positional information identifying each discrete section of the tubular at which each wall measurement was obtained, so that the data may be displayed, presented, analyzed and otherwise used (either by visual means or mathematically) as a three-dimensional object. Another object of the invention is to collect, assemble and/or store wall thickness data of metal tubulars in a form which is susceptible to display, presentation, analysis or other use as a three-dimensional object, including but not limited to display, presentation and analysis as a three-dimensional image which my be viewed from any perspective, zoomed, rotated, each data point individually examined, used in mathematical calculations predicting performance of the tubular under certain conditions, compared with previous or subsequent data and thereby used to project future changes, used in engineering calculations and/or programs which predict response of the tubular to various stressors and otherwise have increased utility.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

In order to practice the invention herein disclosed an ultrasonic means is provided for measuring the wall of small areas of a metal tubular. In preference this will be accomplished by positioning an ultrasonic head in close proximity to the exterior of the tubular and substantially perpendicular to both the longitude and a tangent of the tubular. In preference said head will include an ultrasonic transducer for propagating an ultrasonic wave radially inward (towards the longitudinal axis of the tubular) and for receiving ultrasonic reflections ("echos") returning from the opposite direction. In preference said head will be coupled to the tubular by a medium which effectively transmits ultrasonic waves across the interface between the medium and the tubular, for example by water coupling, or by other means well known in the field of art.

As is well known, by accurately measuring the length of time it takes for the ultrasonic wave to travel from the outer wall of the tubular to the interior wall, reflect from the interior wall and return to the outer wall (known as "time-of-flight" or "TOF"), the distance ("D") the wave has traveled may be readily calculated [from the formula D (distance)=S(speed)× TOF, the speed of sound in various metals being well known]. Wall thickness of the tubular at the area so sampled is one-half of "D".

While those skilled in the art will realize that there are many other practical considerations to obtaining accurate measurement of the wall thickness of a tubular at a particular location by ultrasonic means, including but not limited to, issues relating to ultrasonically coupling the transducer and tubular, issues relating to excluding the effects of coupling from the calculations, issues relating to excluding subsequent reflections from the surfaces, issues relating to accurately "starting" and "stopping" timing measurements in a precise and consistent manner, and, other such issues. As these considerations, and various solutions, are well known to those skilled in the art, they will not be further discussed herein. As it relates to the invention disclosed, it is only necessary that some ultrasonic means be provided to obtain incremental measurements of small, discrete selectable sections of the tubular by ultrasonic means.

In order to practice the invention, a means must also be provided to obtain incremental measurements of small, discrete wall segments throughout the entire area of the tubular of interest (which in most cases will be the entirety of the tubular). In the preferred embodiment this is accomplished by rotating the tubular about its longitudinal axis as the ultrasonic head advances longitudinally along the length of the tubular, and periodically triggering ("firing") the ultrasonic head to make a wall measurement (a "snapshot") of the area of the tubular adjacent thereto at the time. In preference the rate of rotation, longitudinal advance, rate of triggering the ultrasonic head, and size of the ultrasonic head will be such that each snapshot of the wall partially overlaps, both circumferentially and longitudinally with adjacent snapshots, so that complete coverage of the entire area of the tubular to be inspected (which will in most cases be the entire tubular) is obtained. In the preferred embodiment of the invention this is accomplished by disposing the tubular horizontally on a roller system where it may be rotated about its longitudinal axis. In preference the ultrasonic head will be above and adjacent to the upper surface of the horizontally tubular and pointed so as to propagate waves perpendicularly downward toward the tubular. In preference the tubular will be rotated at constant speed, and as it is so rotated, the ultrasonic head advances longitudinally at constant speed, so that the relative movement between the head and the tubular substantially follows a spiral path along the outer surface of the tubular. As the tubular is so advanced the ultrasonic head is periodically fired to take a snapshot of the wall of the tubular. Each of these snapshots is a mathematical representation, a "number", which represents wall thickness of the tubular under the ultrasonic head at the time it is fired. Each of these snapshots will be recorded. Accordingly, at the end of the process a plurality of incremental wall thickness snapshots will have been recorded which represents at least partially overlapping coverage of the entire area of the tubular to be inspected (which will in most cases be the entirety of the tubular).

It will be appreciated by those skilled in the art that a similar result might be obtained by "sampling" (incrementally obtaining data representing small, discrete sections of the wall of a tubular) in a different manner or order. It will be appreciated that the tubular could be disposed other than horizontally during sampling or even disposed in varying positions during sampling. It will be appreciated that sampling might be done by incremental rotation and/or longitudinal advancement and stopping of the tubular, rather than continuous rotation and longitudinal advancement of the tubular (or ultrasonic head) during sampling. It will be appreciated that sampling might be accomplished along a plurality of longitudinal lines about different circumferences of the tubular, or by a plurality of circular lines about different longitudes of the tubular, rather than by sampling along a spiral path. It will be appreciated that the ultrasonic head may be rotated about the tubular rather than the reverse. It will be appreciated that the tubular may be advanced longitudinally with respect to the ultrasonic head rather than the reverse. It will be appreciated that multiple ultrasonic heads may be used. It will be appreciated that sampling may even be accomplished in a random manner. All of these permutations are intended to be comprehended by the invention disclosed herein, the thrust of which does not relate to the particular order in which discrete snapshots of small wall segments of the tubular are obtained and recorded for the entirety of the area of the tubular to be inspected, but that such result is obtained. Namely at the end of the sampling it is desired to have obtained and recorded, with mathematical precision, a plurality of snapshots of the wall of the tubular, each of which represents a wall thickness of a small discrete section of the tubular, in combination with all of the snapshots covering the entire area of the tubular of interest.

In addition to recording discrete snapshots of small sections of the tubular wall over the entire area of the tubular of which is of interest (which in most cases will be the entire tubular), in the invention disclosed herein positional information will also be obtained and recorded as to the location on the surface of the pipe at which each snapshot was taken. In addition thereto, each particular snapshot will be associated with the particular positional information unique to that snapshot.

In the preferred embodiment of the invention, the position of each snapshot of the wall of the tubular is obtained by marking the exterior of the tubular with a longitudinal line which is detectable by photoelectric cell. This line forms a circumferential reference which in the preferred embodiment is treated as a "zero degree" reference. Those skilled in the art will know the reference need not necessarily be considered a zero degree reference, but could in fact be given any other mathematical value (all of which are comprehended by the invention). Each time the tubular is rotated the photoelectric cell is triggered by the reference line. In the preferred embodiment of the invention, each time the cell is triggered the stream of data (representing a stream of discrete wall thickness measurements) is "marked" with an indication that one rotation of the tubular has occurred. In the preferred embodiment of the invention within each rotation each is assigned a numerical value representing the order within that rotation which that particular snapshot was taken (i.e., the first snapshot following triggering of the photoelectric cell will be assigned a value representing 1, the second snapshot assigned a value representing 2, etc.). Those skilled in the art will recognize that any mathematical value could be assigned so long as the assigned value could be subsequently correlated to a circumferential position at which each snapshot could be taken, therefore is comprehended by the invention disclosed herein.

Within each rotation of the pipe the numerical value representing the order in which each snapshot within that revolution of the pipe may of course be converted to a value which represents the angle, from the reference line, at which that snapshot was taken or, in conjunction with knowing the position along the longitude of the tubular at which that rotation occurred, may be converted to some other form (for example, traditional "X, Y, Z" coordinates) which represents the position on the tubular at which each snapshot was taken.

In the preferred embodiment of the invention the data representing one rotation of the pipe is longitudinally synchronized with snapshots of another revolution of the tubular, so that accurate alignment of data along a longitude is maintained, even if speed of rotation of the tubular was not exactly the same in one rotation as another rotation, or other conditions have occurred where the number of snapshots in one revolution of the tubular is not exactly the same as the number of snapshots in other revolutions. In the preferred embodiment of the invention, synchronizing the circumferential data once each revolution of the tubular has been found adequate. In the preferred embodiment of the invention, synchronization is accomplished by computer means which converts the value which represents the order in a particular revolution pertaining to each snapshot to a value which represents angular position of each snapshot about the circumference of the tubular. Thus, if in one revolution there were 400 data points (each of which represented a wall thickness reading, or "snapshot"), the 100th data point will be converted to a value which will interpreted to be 90° from the reference marking, the 200th data point converted to a value representing 180° from the reference marking, etc. Whereas if in a different revolution there are 500 data points, then the 125th data point will be converted to a value which will be interpreted to be 90° from the reference marking, the 250th data point converted to a value representing 180° from the reference marking, etc. In this way all the data points in one rotation of the tubular are longitudinally synchronized with all data points corresponding longitudinally in other revolutions of the tubular. It will be appreciated that synchronization of data could be accomplished more frequently or less frequently than once each revolution, or by means other than use of an external reference line detectable by a photoelectric cell. It will be appreciated that instead of converting position of the discrete snapshots about the circumference of the tubular into angular format, said position could be represented as a point in any coordinate system. For purposes of the invention disclosed herein it does not matter how the position about the circumference of the tubular that each of the discrete snapshots of the wall thickness is mathematically represented, but rather that such circumferential information about each snapshot is obtained and recorded with mathematical precision.

In the preferred embodiment of the invention not only will circumferential position of each wall thickness measurement ("snapshot") be obtained, but longitudinal position of each snapshot will also be obtained, recorded and associated, with mathematical precision, to each discrete snapshot. In the preferred embodiment of the invention it is the ultrasonic head which moves along a line parallel to the axis of the tubular during inspection thereof. In the preferred embodiment of the invention a sensor on said head generates a signal as to its position along the longitude of the tubular each time the transducer is fired. Thus in the preferred embodiment this signal is recorded each time the head is fired (to take a wall thickness reading, a "snapshot" of the wall). Those skilled in the art will recognize that longitudinal position of each snapshot might be obtained by other means, including but not limited to measuring the relative speed of longitudinal movement between the tubular and ultrasonic head as a function of time, counting the number of revolutions it takes for a tubular to advance a certain distance in respect to the head and thereby calculating the point along the spiral path which each snapshot was taken, or other means. For purposes of the invention disclosed herein the particular manner of obtaining the longitudinal position at which each wall thickness snapshot is taken is not important, but rather that such data is obtained, recorded and associated with each snapshot, with mathematical precision. Accordingly at the conclusion of the process there will have been obtained and recorded a plurality of overlapping measurements of small discrete sections of the wall of the tubular. Each measurement will include a mathematically precise representation of wall thickness and be associated with a mathematically precise three-dimensional representation the place on the tubular where that measurement of the wall was obtained from. The plurality of such readings will cover the entire area of the wall of interest, which in most case may be the entire tubular.

It will however be appreciated that the invention is not so limited. Namely the entire area of the tubular need not necessarily be sampled. Rather by appropriately triggering the ultrasonic head to fire only between certain areas of the rotation of the tubular one might limit inspection to the longitudinal weld line of the pipe. Alternatively the ultrasonic head may be adjusted to fire only at certain longitudinal positions of the pipe, thus, for instance limit inspection to certain areas along the length of the pipe. Alternatively both might be the ultrasonic head may be set to only within certain circumferential or longitudinal limits, defining a relatively small section of the pipe to be inspected according to the invention. Such permutations are fully comprehended by the invention.

It will also be appreciated that sampling according to the invention need not necessarily be of contiguous areas of the pipe, or comprise overlapping snapshots. It is comprehended that the invention may be utilized with spaces between snapshots. While leaving spaces between snapshots may fail to reveal a small defect in the space not sampled, the data gathered by the invention will still form that of a virtual three-dimensional object which has utility, for instance in simulative and modeling programs, far above that currently available.

So far as synchronization of longitudinal data, such synchronization has not been found necessary if the tubular is rotated according to the preferred embodiment discussed above, because while there are a plurality of rotations of the tubular (which may require synchronization as discussed above), there is only one longitudinal advancement of the tubular. Accordingly there is no plurality of discrete sets of data, each representing a discrete longitude of the tubular, to be synchronized with other data also representing a longitude of the tubular. This would be different if the data were gathered or recorded in a different manner which resulted in different sets of data, each of which said sets represented a longitude of the tubular. In this instance, it would be desirable to convert the number of data points in each set to correspond to the known length of the tubular, so that the discrete sets of longitudinal data would correspond to that length and therefore each other. Accordingly, comprehended by the invention herein is circumferential and/or longitudinal synchronization of data, as may be necessary.

In the preferred embodiment of the invention, effective size of the transducer is about one-half inch in diameter. Accordingly, in the preferred embodiment of the invention, to assure full coverage of the area of interest in the preferred embodiment described above, a rate of rotation and triggering of the transducer is selected so that the transducer each triggered as the tubular rotates about ⅜th inch (or less), and each rotation of the tubular results in a longitudinal advancement of the tubular about ⅜th inch (or less). It will be appreciated by those skilled in the art that rate of rotation and advancement would vary if a transducer of different size were used, the objective being to assure snapshots which partially overlap. It will be appreciated that the smaller the effective area of the ultrasonic head the finer resolution of wall thickness will be obtained, but at the sacrifice of speed and accumulation of larger amounts of data.

It may be appreciated that since in the preferred embodiment of the invention each snapshot (representing measurement of wall thickness of the tubular at a discrete location) at least partially overlaps adjacent snapshots, at least where such overlap occurs there may be two, possibly more, measurements of wall thickness. It may be also appreciated that the measurements may not be exactly the same, since each covers at least a portion of the surface that the adjacent snapshot does not cover. It may be appreciated that where such overlap occurs and is not identical, there is presented an ambiguity as to the value to be assigned the wall thickness where such overlap occurs. In the preferred embodiment of the invention it is the value which represents the smallest ("thinnest") wall thickness which is assigned this area, because a thin wall condition is believed to represent the greatest risk of failure of the tubular. However, this does not have to be so. The value which represents the thickest wall section could as easily be used, or an average between the multiple reading could be assigned to the area where such overlap occurs. All are comprehended by the invention herein disclosed.

Accordingly, in the preferred embodiment of the invention, partially overlapping wall thickness measurements representing discrete, incremental, overlapping measurements of small areas of the tubular as well as positional information of each discrete measurement of wall thickness will be obtained and will be associated with each other. In the preferred embodiment of the invention the requisite association of each discrete measurement of wall thickness with the positional information pertaining to that measurement is accomplished by digital means. That is both measurement of wall thickness and positional information are converted to digital format appended together as one data point. Those skilled in the art will recognize that other forms of association, including but by not limited to use of cross-reference table, would also work. For purpose of the invention the manner that each discrete measurement of wall thickness is associated with respective positional information is not of particular importance, only that such association be made. It is however particularly useful (while the invention is not limited thereby) that such data be associated in a form that is readable by computer means, in order to facilitate computer display, analysis and use of the information.

Data contained in such format may be used in ways not previously possible. For instance, the data representing wall thickness may be, by computer means, shade and/or color coded and presented in virtual three-dimensional form, which clearly resembles visual inspection of the tubular, or sections of particular interest, from almost any perspective, from any apparent distance, with or without enlargement, as if the walls of the tubular were color and/or shaded coded (different thicknesses represented different colors and/or shades).

Moreover, the precise numerical value of the thickness of any section and its precise location on the tubular, may be obtained from such presentation. While the preferred embodiment of the invention uses "Open GL" computer graphic rendering software to display the tubular data, those skilled in the art will recognize that other computer graphic rendering software could be used as well.

Moreover the data contained in digital format which represents wall thickness of each incremental section of a tubular and the location of that section can be used in computations which predict the actual effect on the tubular to various stressors, including tensile, bending, collapse and burst forces, aging, etc. Particularly useful by sequential inspection of a tubular, is the ability to analyze changes which have occurred over a period of time, and thereby be able to accurately predict, prior to failure of the tubular, when failure is likely to occur, thereby avoid same, but at the same time maximize use of the tubular.

In addition to the discussion above, the data can be associated with other measurements of the tubular which may be of interest. For instance other means, such as cam following means, ultrasonic means, laser means, and other means for collecting pertaining to ovality of the tubular can also be associated with wall thickness data, positional information or both. Likewise, not only may wall thickness and ovality data be associated with positional information, but data derived from other means (typically ultrasonic means generating "sheer waves") designed to detect defects within the wall of the tubular, such as inclusions, voids, delaminations, etc. may also be associated with positional data. By so doing this other information would thereby become subject to display, presentation, analysis or other use as three-dimensional data.

It is thus to be appreciated that a process established in accordance with the principles and teachings of the present inventive disclosure constitutes an advancement in the field of art to which the invention pertains. While the above description contains many specificities, these should not be construed as limitations on the scope of the invention, but rather as an exemplification of preferred embodiments thereof. Accordingly, the scope of the present invention should be determined not by the embodiments illustrated, but by such claims as may be allowed and their legal equivalents.

The invention claimed is:

1. Method for predicting performance of tubular goods, comprising:
   a. positioning an ultrasonic detection means which is capable of measuring the thickness of a discrete section of the wall of a tubular good in a plurality of adjacent, partially overlapping sampling positions spaced longitudinally and circumferentially along an area to be inspected of the wall of a tubular good;
   b. at each sampling position, causing said ultrasonic detection means to determine the thickness of a discrete portion of the wall of said tubular good;
   c. for each sampling position, determining the longitudinal position of said ultrasonic detection means along the axis of said tubular good and the circumferential position of said ultrasonic detection means about the circumference of said tubular good;
   d. recording the measurements of wall thickness in an associated relationship with their corresponding longitudinal positions and circumferential positions to form a computer-readable, three dimensional representation of the wall of the tubular good over the area to be inspected; and
   e. using the three-dimensional representation in computations to predict the effect of specific stress conditions on the tubular good.

2. The method of claim 1 wherein said stress conditions comprise at least one of tensile, bending, collapse, aging and burst forces.

3. The method of claim 2 wherein said computations further comprise data as to ovality of the tubular good.

4. The method of claim 3 wherein said area of interest comprises the entire wall of the tubular good.

5. The method of claim 4 wherein said step (a) comprises advancing the ultrasonic detection means and the wall of the tubular good longitudinally relative to one another while rotating the tubular good about its longitudinal axis.

6. The method of claim 5 wherein in step (b) the ultrasonic detection means is triggered periodically to generate a stream of discrete wall thickness measurements following a substantially helical path on the wall of the tubular good, while detecting and marking in the stream of measurements each complete rotation of the tubular good.

7. The method of claim 6 wherein determining the circumferential position in step (c) comprises converting the position of a measurement in the stream to a representation of its circumferential position by reference to the number of measurements made in a complete rotation containing that measurement.

8. The method of claim 7 further comprising repeating the steps (a) to (f) for sequential inspection of the same tubular good and analyzing changes which have occurred over a period of time to predict when failure is likely to occur, and to avoid failure while maximizing use of the tubular good.

9. The method of claim 8 applied to the inspection of tubular goods for use in oil and gas exploration or production.

10. The method of claim 2 wherein said area of interest comprises the entire wall of the tubular good.

11. The method of claim 10 wherein said step (a) comprises advancing the ultrasonic detection means and the wall of the tubular good longitudinally relative to one another while rotating the tubular good about its longitudinal axis.

12. The method of claim 11 wherein in step (b) the ultrasonic detection means is triggered periodically to generate a stream of discrete wall thickness measurements following a substantially helical path on the wall of the tubular good, while detecting and marking in the stream of measurements each complete rotation of the tubular good.

13. The method of claim 12 wherein determining the circumferential position in step (c) comprises converting the position of a measurement in the stream to a representation of its circumferential position by reference to the number of measurements made in a complete rotation containing that measurement.

14. The method of claim 13 further comprising repeating the steps (a) to (f) for sequential inspection of the same tubular good and analyzing changes which have occurred over a period of time to predict when failure is likely to occur, and to avoid failure while maximizing use of the tubular good.

15. The method of claim 14 applied to the inspection of tubular goods for use in oil and gas exploration or production.

16. The method of claim 1 wherein said area of interest comprises the entire wall of the tubular good.

17. The method of claim 16 wherein said step (a) comprises advancing the ultrasonic detection means and the wall of the tubular good longitudinally relative to one another while rotating the tubular good about its longitudinal axis.

18. The method of claim 17 wherein in step (b) the ultrasonic detection means is triggered periodically to generate a stream of discrete wall thickness measurements following a substantially helical path on the wall of the tubular good, while detecting and marking in the stream of measurements each complete rotation of the tubular good.

19. The method of claim 18 wherein determining the circumferential position in step (c) comprises converting the position of a measurement in the stream to a representation of its circumferential position by reference to the number of measurements made in a complete rotation containing that measurement.

20. The method of claim 19 further comprising repeating the steps (a) to (f) for sequential inspection of the same tubular good and analyzing changes which have occurred over a period of time to predict when failure is likely to occur, and to avoid failure while maximizing use of the tubular good.

21. The method of claim 20 applied to the inspection of tubular goods for use in oil and gas exploration or production.

\* \* \* \* \*